(12) United States Patent
Tateishi et al.

(10) Patent No.: US 9,943,495 B2
(45) Date of Patent: Apr. 17, 2018

(54) COMPOSITION CONTAINING DIHOMO-γ-LINOLENIC ACID (DGLA) AS THE ACTIVE INGREDIENT

(71) Applicant: SUNTORY HOLDINGS LIMITED, Osaka (JP)

(72) Inventors: Norifumi Tateishi, Ibaraki (JP); Hiroshi Kawashima, Takatsuki (JP)

(73) Assignee: SUNTORY HOLDINGS LIMITED, Osaka-shi, Osaka (JP)

(*) Notice: Subject to any disclaimer, the term of this patent is extended or adjusted under 35 U.S.C. 154(b) by 0 days.

(21) Appl. No.: 14/644,231

(22) Filed: Mar. 11, 2015

(65) Prior Publication Data
US 2015/0182486 A1 Jul. 2, 2015

Related U.S. Application Data

(63) Continuation of application No. 11/884,199, filed as application No. PCT/JP2006/302787 on Feb. 10, 2006, now Pat. No. 9,006,287.

(30) Foreign Application Priority Data

Feb. 14, 2005 (JP) .................. 2005-036235
Apr. 28, 2005 (JP) .................. 2005-133264
Apr. 28, 2005 (JP) .................. 2005-133271

(51) Int. Cl.
*A61K 31/202* (2006.01)
*A61K 31/232* (2006.01)
(Continued)

(52) U.S. Cl.
CPC .......... *A61K 31/202* (2013.01); *A23L 33/12* (2016.08); *A61K 31/232* (2013.01); *A61K 31/66* (2013.01); *A23V 2002/00* (2013.01)

(58) Field of Classification Search
CPC .......... A23V 2002/00; A23V 2200/318; A23V 2250/1874; A23L 1/3008; A61K 31/202; A61K 31/232; A61K 31/66
See application file for complete search history.

(56) References Cited

U.S. PATENT DOCUMENTS

| 4,309,415 A | 1/1982 | Horrobin |
| 4,444,755 A | 4/1984 | Horrobin |

(Continued)

FOREIGN PATENT DOCUMENTS

| CN | 1438884 A | 8/2003 |
| EP | 0003407 A1 | 8/1979 |

(Continued)

OTHER PUBLICATIONS

Iversen et al., "Linoleic acid and dihomogammalinolenic acid inhibit leukotriene B4 formation and stimulate the formation of their 15-lipoxygenase products by human neutrophils in vitro. Evidence of formation of antiinflammatory compounds," Agents and Actions, Jul. 1991, vol. 333, No. 3-4, pp. 286-291.

(Continued)

*Primary Examiner* — Savitha M Rao
(74) *Attorney, Agent, or Firm* — Drinker Biddle & Reath LLP

(57) ABSTRACT

The present invention provides a composition, such as a food and pharmaceutical agent, which comprises dihomo-γ-linolenic acid, and which has the effect of preventing or treating skin diseases; a composition such as a food and pharmaceutical agent which comprises dihomo-γ-linolenic acid and which has the effect of preventing or treating skin diseases; and a composition which comprises dihomo-γ-linolenic acid and which has the effect of preventing or treating diseases related to increased mast cell count.

9 Claims, 2 Drawing Sheets

(51) Int. Cl.
A61K 31/66 (2006.01)
A23L 33/12 (2016.01)

(56) References Cited

U.S. PATENT DOCUMENTS

| | | | |
|---|---|---|---|
| 4,681,896 A | 7/1987 | Horrobin | |
| 2003/0013759 A1 | 1/2003 | Das | |
| 2004/0208939 A1 | 10/2004 | Sears et al. | |

FOREIGN PATENT DOCUMENTS

| | | | |
|---|---|---|---|
| EP | 019423 A1 | 11/1980 | |
| EP | 0155419 A2 | 9/1985 | |
| EP | 0334507 A2 | 9/1989 | |
| EP | 0416855 A2 | 3/1991 | |
| EP | 0535940 A1 | 4/1993 | |
| EP | 0713653 A1 | 5/1996 | |
| EP | 0992236 A1 | 4/2000 | |
| EP | 1319402 A1 | 6/2003 | |
| EP | 1852114 A1 | 11/2007 | |
| JP | 55-27168 A | 2/1980 | |
| JP | 59-152324 | 8/1984 | |
| JP | 2-149508 | 6/1990 | |
| JP | 3099013 A | 4/1991 | |
| JP | 4-244023 | 9/1992 | |
| JP | 6-128154 | 5/1994 | |
| JP | 6197735 A | 7/1994 | |
| JP | 2002-47176 | 2/2002 | |
| JP | 2006219454 A | 8/2006 | |
| JP | 2006306812 A | 11/2006 | |
| JP | 2006306813 A | 11/2006 | |
| WO | WO-9508349 A1 | 3/1995 | |
| WO | WO-02/02105 A | 1/2002 | |

OTHER PUBLICATIONS

Rand et al., "Arachidonic Acid Metabolism of the Murine Eosinophil. II. Involvement of the Lipoxygenase Pathway in the Response to the Lymphokine Eosinophil Stimulation Promoter," J. Immunol., Sep. 1982, vol. 129, No. 3, pp. 1239-1244.
Thompson-Snipes et al., "Interleukin 10: A Novel Stimulatory Factor for Mast Cells and Their Progenitors," J. Exp. Med, Feb. 1, 1991, vol. 173, No. 2, pp. 507-510.
Moore et al., "Interleukin-10," Annu. Rev. Immunol, 1993, vol. 11, pp. 165-190.
Office Action dated May 24, 2011 in JP 2005-133264.
Office Action dated May 24, 2011 in JP 2005-133271.
Office Action dated May 24, 2011 in JP 2005-036235.
Office Action dated May 8, 2012 in JP 2012-1473.
Ziboh, "Essential Fatty Acids/Eicosanoid Biosynthesis in the Skin: Biological Significance," Society for Experimental Biology and Medicine, vol. 205, 1994, No. 1, pp. 1-11.
Ziboh et al., "Dihomo-γ-Linolenic Acid/15-Hydroxyeicosatrienoic Acid in Skin Inflammatory and Proiferative Processes," γ-inolenic Acis: Recent Advances in Biotechnology and Clinical Applications, 2000, pp. 198-206.
Miller et al., "Gammalinolenic Acid-Enriched Diet Alters Cutaneous Eicosanoids," Biochemical and Biophysical Research Communications, vol. 154, No. 3, 1988, pp. 967-974.
Office Action dated Jun. 19, 2012 in Canadian Patent Application No. 2,599,112.
Office Action issued in corresponding Japanese Patent Application No. 2005-36235 dated Jan. 7, 2014.
Brenner (Biooriginal, Sep. 2003, retrieved from internet on Mar. 4, 2010, URL:http:///www.biorginal.com/services/files/file_42.pdf.
Office Action issued by Chinese Patent Office in Chinese Application No. 2006100031128, dated Dec. 4, 2009.
Buske-Kirschbaum et al., Psychotherapy and Psychosomatics, 2001, vol. 70, pp. 6-16.
Novak et al., Journal of Allergy Clinical Immunology, vol. 112, Issue 6, 2003, pp. S128-S139.
Karmali, Rashida A., "Effect of Dietary Fatty Acids on Experimental Manifestation of *Salmonella*-Associated Arthritis in Rats," Prostaglandins, Leukotrienes and Medicine, 1987, pp. 199-204, vol. 29. No. 2/3, United Kingdom.
Dooper, Maaike M.B.W. et al., "Dihomo-γ-Linolenic Acid Inhibits Tumor Necrosis Factor-α Production by Human Leucocytes Independently of Cyclooxygenase Activity," Immunology, 2003, pp. 348-357, vol. 110, Blackwell Science Ltd., Oxford, England.
Search Report dated Mar. 20, 2006 for International Application No. PCT/JP2006/302787 filed Feb. 20, 2006.
Nissen et al., "γ-Linolenic acid in the oil decreases skin roughness and TWEL and increases skin moisture in normal and irritated skin," Cosmetics & Toiletries Magazine, vol. 110, Oct. 1995, pp. 71-76.
Santoli et al., "Prostaglandin E Precursor Fatty Acids Inhibit Human IL-2 Production by a Prostaglandin E-Independent Mechanism," The Journal of Immunology, vol. 143, No. 4, Aug. 15, 1989, pp. 1303-1309.
Iverson et al., "Effect of dihomogammalinolenic acid and its 15-lipoxygenase metabolite on eicosanoid metabolism by human mononuclear leukocytes in vitro: selective inhibition of the 5-lipoxygenase pathway," Arch. Dermatol. Res. (1992), 284; pp. 222-226.
Zurler et al., "Human peripheral blood T lymphocyte proliferation after activation of the T cell receptor: effects of unsaturated fatty acids," Prostaglandine, Leukotrianes and Essential Fatty Acids, (1999), 60(5&6), pp. 371-375.
Horrobin, "Essential fatty acid metabolism and its modification in atopic eczema," Am. J. Clin. Nutr. 2000, 71 (suppl.); pp. 367S-372S.
Manku et al., "Reduced Levels of Prostaglandin Precursors in the Blood of Atopic Patients: Defective Delta-6-Desaturase Function as a Biochemical Basis for Atopy," Prostaglandine Leukotrienes and Medicine 9; 1982, pp. 615-628.
Wright et al., "Oral Evening-Primrose-Seed Oil Improves Atopic Excema," The Lancet, Nov. 20, 1982, p. 1120.
Hamada, "Abstract of the 50th General Meeting of the Japanese Society of Allergology," 2000, pp. 999 [partial translation].
Navarette et al., "Dietary Intake of Concentrated Gamma-Linolenic Acid (GLA)-Enriched Oil Supresses Cutaneous Level of Dihomo-Gamma-Linolenic Acid (DGLA): Possible in vivo Inhibition of Microsomal Elongation of GLA to DGLA," Prostaglandins Leukotrienes and Essential Fatty Acids, (1992), 46, pp. 139-144.
Henz et al., "Double-blind, multicentre analysis of the efficacy of borage oil in patients with atopic eczema," British Journal of Dermatology, 1999, 140; pp. 685-688.
Hiroi et al., "Effect of Tacrolimus Hydrate (FK506) Ointment on Spontaneous Dermatitis in NC/Nga Mice," Jpn. J. Pharmacol., 76, 1998, pp. 175-183.
Yoshida, "Journal of the Oto-Rhino-Laryngological Society of Japan," (Nippon Jibiinkoka Gakkai Kaiho), 2001, pp. 104-504.
Bradding, "The role of the mast cell in asthma: a reassessment," Mechanisms of allergy and adult asthma, 2003, 3, pp. 45-50.
Yamamoto, "Allergy," 2004, 49: 45 [partial translation].
Chika Horikawa et al., "On Lipid Metabolism in Vivo of Dietary Dihomo-γ-linolenic Acid in Guinea Pigs (Report No. 3)," The Japanese Society of Nutrition and Food Science Sokai Koen Yoshishu, 2004, p. 219, vol. 59 [English translation].
Willis et al.,"Dihomo-gamma-linolenic and gamma-linolenic acids in health and disease" In New protective roles for selected nutrients, Ed Alan R. Liss, New York,1989, 39-108.
EP Application 0713928.7—Office Action dated Sep. 28, 2015.

COMPOSITION CONTAINING DIHOMO-γ-LINOLENIC ACID (DGLA) AS THE ACTIVE INGREDIENT

This is a Continuation of copending application Ser. No. 11/884,199, filed Aug. 13, 2007, which is a PCT National Stage of PCT/JP2006/302787 filed Feb. 10, 2006, which claims priority to JP Application No. 2005-133271 filed Apr. 28, 2005; JP Application No. 2005-133264 filed Apr. 28, 2005; and JP Application No. 2005-036235 filed Feb. 14, 2005.

TECHNICAL FIELD

The present invention relates to a food ingredient having a preventive or therapeutic effect on various skin diseases including allergic dermatitis, such as atopic dermatitis and contact dermatitis, eczema, and UV-derived skin disorders, or a food composition comprising said ingredient. More specifically, it is intended to provide an optimum dosage for exhibiting the effect of the ingredient to the fullest.

The present invention also relates to a food ingredient having a preventive or therapeutic effect on various diseases such as skin diseases, respiratory system diseases and digestive system diseases that are closely related to eosinophil infiltration and increased cell counts, or a food composition or pharmaceutical composition comprising the ingredient, and in particular to an inhibitor of eosinophil infiltration.

Furthermore, the present invention relates to a food ingredient having a preventive or therapeutic effect on various disease conditions such as atopic dermatitis, bronchial asthma, pollinosis, allergic rhinitis and allergic conjunctivitis in which mast cell count are enhanced specifically in the lesion, or a food composition or a pharmaceutical composition comprising the ingredient, and in particular to an inhibitor of enhancement in mast cell count.

BACKGROUND ART

In the classification of a variety of fatty acids from a structural viewpoint, those having a long fatty acid chain comprising about 20 carbons in the molecule and containing two or more unsaturated sites (double bonds) are termed as polyunsaturated fatty acids (PUFAs). Alternatively, based on its extreme significance for the maintenance of human health from a nutritional viewpoint, some fatty acids are often expressed as essential fatty acids (EFAs). The definition of EFA signifies, in a narrow sense, linoleic acid (LA) and α-linolenic acid (ALA) that cannot be synthesized by humans and thus must be ingested through food, and in a broad sense, it also includes their metabolites, arachidonic acid (AA), eicosapentaenoic acid (EPA) and docosahexaenoic acid (DHA). Among them, a series of fatty acids produced with ALA as the parent fatty acid are termed as n3-series PUFAs, which include EPA and DHA.

On the other hand, as shown in FIG. 1, similar fatty acids produced with LA as the parent fatty acid are termed as n6-series PUFAs, in which, specifically, LA is metabolized by Δ6-desaturase to γ-linolenic acid (GLA), then by a carbon-chain elongase to DGLA, and further by Δ5-desaturase to AA.

The physiological role of these n6-series PUFAs have been extensively studied, and GLA, among them, has been demonstrated to be useful in skin disorders (Cosmetic & Toiletries, Nissen H P, 1995, 119: 71), diabetes mellitus and its complications (Diabetic Medicine, Jamal G A, 1990, 7: 319), rheumatoid arthritis (Arthritis Rhermatism, Zurier R B, 1996, 39: 1808) and the like. In connection with the molecular mechanism in the physiological function of GLA, it has been proposed, as shown in FIG. 1, that the active molecule is DGLA which is a carbon chain-elongated metabolite of GLA, the 1-series prostaglandin (PG1) which is a cyclooxygenase metabolite of DGLA, or 15-hydroxyeicosatrienoic acid (15-HETrE) which is a lipoxygenase metabolite of DGLA.

On the other hand, on the physiological activity of DGLA, part of the effect has been confirmed in vivo or in vitro: in vivo, effects of inhibiting platelet agglutination (British Medical Journal, Kernoff P B A, 1977, 2: 1441), delayed-type footpad edema (Lipids, Taki H., 1993, 28: 873), blood pressure increase (Lipids, Cedric H., 1984, 19: 699) and other effects have been reported, and in vitro, effects of inhibiting the production of cytokines such as interleukin-2, -10 and tumor necrosis factor (TNF-α) (Immunology, Maaike M B W D, 2003, 110: 348; The Journal of Immunology, Deniela S, 1989, 143: 1303), leukotriene production (Archives of Dermatological Research, Iversen L, 1992, 284: 222), and T cell growth (Prostaglandin Leukotrienes and Essential Fatty Acids, Zurier R B, 1999, 60: 371) and other effects have been reported.

The relationship of the physiological functions of living organisms (in particular, the skin) and PUFAs have been investigated in various fields. For example, it has been demonstrated that when animals such as rats are kept under an EFA-deficient condition for a long period of time, they may develop skin scale, decreased moisture, increased moisture loss and the like, and specifically abnormal skin functions. It is also suggested that PUFAs are deeply involved in various skin diseases such as eczema, contact dermatitis and UV-derived skin damages. Furthermore, GLA is useful in the prevention and treatment of various diseases, as described above, and among them, it has been proved, GLA is useful in skin diseases, specifically in atopic dermatitis (American Journal of Clinical Nutrition, Harrobin D F, 2000, 71: 367).

At first, it was found that in the serum of patients with atopic dermatitis, the amount of LA in the serum is increased as compared to normal healthy subjects, and conversely, at that time, the amounts of DGLA and AA that are metabolites from LA were found to be decreased. This fact strongly suggests the possibility that the function of Δ6-desaturase, an enzyme that converts LA to GLA, in the n6-series PUFA metabolic pathway is decreased in patients with atopic dermatitis.

Thus, it can be estimated that the ingestion of PUFAs which are located downstream to the Δ6-desaturase can improve diseases accompanied by abnormal PUFA metabolism, and it was investigated whether the ingestion of GLA, among them, which is relatively abundant in nature and abundant in the seeds of *Oenothera, Ribes nigrum* and *Borrago officinalis* can improve various conditions of atopic dermatitis.

As a result, it was reported in a human study that the oral ingestion of GLA (about 180-1440 mg/person/day) can improve the skin inflammation conditions or itching sensations of atopic dermatitis, and specifically it was more effective in patients who took a high dose of 720 or 1440 mg/person/day. The finding at the time confirmed that GLA can effectively increase the amounts of DGLA and AA in the living body, more effectively the amount of DGLA, and that there is a positive correlation between the improvement in disease conditions and DGLA (Prostaglandins Leukotrienes and Medicine, Mauku M S, 1982, 9: 615; The Lancet, Wright S, 1982, 20: 1120).

The effectiveness of GLA has also been confirmed in NC/Nga mice, an animal model of atopic dermatitis, and the oral ingestion of GLA (about 1250 mg/kg/day) has also been found to have effects of inhibiting the formation of atopic dermatitis and IgE production (Abstract of the 50th General Meeting of the Japanese Society of Allergology, Zui Hamada, 2000, pp. 999). As described above, the ingestion of GLA, among the n6-series PUFAs, is effective for the improvement of atopic dermatitis, and it has been estimated that preferably the ingestion of DGLA that is believed to be the active substance is more effective.

However, there remains a possibility that the appropriate establishment of an optimum dosage has not been made in GLA ingestion intended for the correction of abnormal PUFA metabolism such as atopic dermatitis mentioned above. In guinea pigs, a phenomenon was observed that the dosage and the amount increased of PUFAs in the living body does not correlate, i.e. in the administration of GLA at a highly excessive amount of about 3200 mg/kg/day, the amount of DGLA in the epidermis decreased as compared to that when about 400 mg/kg/day of GLA was ingested (Prostaglandins Leukotrienes and Essential Fatty Acids, Navarette R, 1992, 46: 139). This suggests a possibility that the ingestion of a large amount of GLA may inhibit the conversion of GLA to DGLA.

Thus, when a large amount of GLA is ingested, the amount of DGLA in the living body may tend to decrease rather than to increase, posing a risk of aggravating atopic dermatitis. Furthermore, it is known that there exists an individual difference in the metabolism of GLA in humans. When GLA was administered to human patients with atopic dermatitis, the degree of enhancement in the amount of DGLA in the erythrocyte membrane varied with individuals, and in the patient group having enhancement in the amount of DGLA the dermatitis condition improved, whereas no improvement was noted in the patient group having no enhancement in the amount of DGLA (British Journal of Dermatology, Henz B M, 1999, 140: 685). This means that the ingestion of GLA is not necessarily effective for increasing the amount of DGLA, and that in the treatment of atopic dermatitis, the optimum amount of GLA may not be the optimum amount of DGLA.

On the other hand, it has been confirmed that the ingestion of DGLA leads to increases in the amount of DGLA in the living body in a dose dependent manner (Abstract of the 58th Meeting of the Japanese Society of Nutrition and Food Science, Chika Horikawa, 2004, pp. 219), and thus even if DGLA was ingested in a large amount, it is hard to conceive that the amount of DGLA in a living body decreases. Furthermore, in the inhibition of metabolic enzymes by GLA described above, originally the activity of the enzyme is considered to be relatively high, which indicates a possibility that carbon-chain elongation enzymes possibly free of activity reduction due to aging may be affected by the substrate environment or other factors as long as they participate in enzyme reactions.

As a result, it is likely that the amount of DGLA when GLA was ingested may vary depending on various conditions, which strongly suggests the difficulty of appropriately controlling the treatment of atopic dermatitis by the ingestion of GLA. Thus, from the viewpoint of safety and effectiveness, the direct ingestion of DGLA per se is more preferred than the ingestion of GLA in the treatment or prevention of atopic dermatitis, in which it is further considered to be very important to provide an optimum dosage.

However, some meat, eggs and seafoods contain DGLA, but they are limited in the number of types, and for vegetarians, ingestion of DGLA from natural products is very difficult. Furthermore, DGLA occurs in nature, but the amount is very limited and mass production is difficult, and thus it is very difficult to demonstrate its effect on atopic dermatitis using DGLA as in the GLA study mentioned above. However, as far as we know, there is no direct demonstration that atopic dermatitis is improved by DGLA per se, and though DGLA has been demonstrated to have various physiological effects in in vivo tests or in vitro tests using various animal- or human-derived cell lines, as described above, none of the tests are considered to simulate atopic dermatitis, and thus there is no definite answer to whether DGLA can improve atopic dermatitis or not.

As shown in Japanese Patent No. 3354581, by inventing a method of obtaining microorganisms deficient in $\Delta 5$-desaturase and producing DGLA lipids by fermentation of the microorganisms, the present inventors have enabled mass production of a triglyceride SUNTGD of which about 40% of constituent fatty acids comprises DGLA, and thus have overcome the previous difficulties in obtaining the raw material of DGLA.

In recent years, it has been demonstrated that eosinophil infiltration occurs at inflammatory regions in various diseases including skin diseases such as atopic dermatitis, eczema and psoriasis, respiratory system diseases such as bronchial asthma, chronic obstructive pulmonary disease (COPD), hypersensitivity pneumonitis and eosinophilic pneumonitis, and digestive system diseases such as eosinophilic gastroenteritis and ulcerative colitis, and thus eosinophils have been implicated to be deeply involved in the formation and progression of these disease conditions. Under these circumstances, attempts have been made to prevent and/or treat these diseases by inhibiting the steps of eosinophil infiltration into the tissues of the lesion, specifically eosinophil activation, adhesion to the endothelium, extravascular migration, and movement of chemotactic factors into the lesion (American Journal of Clinical Dermatology, Chari S, 2001, 2: 1; Paediatric Respiratory Reviews, McMillan R M, 2001, 2: 238; Agents Actions, Rask-Madsen J, 1992, C37; Japanese Unexamined Patent Publication (Kokai) No. 8-3036).

For example, it has been found that steroid external preparations and immunosuppressive external preparations for which clinical usefulness has been confirmed for the treatment of skin diseases can alleviate the aggravation of skin conditions in an atopic dermatitis animal model, NC/Nga mice, and also to suppress significantly the number of eosinophils infiltrating into the skin lesions (Japanese Journal of Pharmacology, Hiroi J, 1998, 76: 175). Also, as a substance that is a chemotactic factor having a property of accumulating eosinophils into the lesions, leukotriene B4 can be mentioned, and this substance has been found to be synthesized by 5-lipoxygenase.

In contrast, 5-lipoxygenase inhibitors suppress the production of leukotriene B4 by inhibiting the activity of this enzyme, and also suppress the subsequent biological event of eosinophil infiltration. As a result, it has been found, the compounds can alleviate respiratory disorders of nocturnal asthma in which leukotrienes and eosinophils are deeply involved, indicating their usefulness in respiratory system diseases (American Journal of Respiratory and Critical Care Medicine, Wenzel S E, 1995, 152: 897). Thus, these pharmaceutical drugs have been demonstrated to be useful in the prevention and/or treatment of various diseases by controlling abnormal eosinophil conditions, whereas there are problems with safety and the methods for using them.

There are side effects in using steroid external preparations, such as blushing and atrophy of the skin during use and the rebound phenomenon in which the suspension of administration may aggravate dermatitis, whereas immunosuppressive external preparations may facilitate skin tumors and their efficacy is greatly affected by the application site and the state of the barrier function of the skin (Journal of the Japanese Dermatological Association, Masutaka Furue, 2004, 114: 135), and 5-lipoxygenase inhibitors must be orally administered as many as four times a day and their ingestion over a long period of time may cause dyspepsia (ZYFLO™ FLIMTAB™, package insert, Abbott Laboratories, 1998).

Under these circumstances, materials have long been sought that are medically useful, which can be used safely by everyone, and can effectively inhibit the function of eosinophils.

Considering medically or nutritionally useful food ingredients, there can be mentioned eicosapentaenoic acid (EPA) or docosahexaenoic acid (DHA) that are n3-series polyunsaturated fatty acids as shown in FIG. 2 as one of the candidate materials. These ingredients are relatively abundant in marine animal oils, specifically fish oils such as bonito and sardine oils, which have been ingested by mankind for a long period of time and are naturally very safe. Also, extensive studies have been made on the physiological functions thereof, and such usefulness has been found as the effect of inhibiting blood clots for the former and as the effect of enhancing the learning function has been demonstrated for the latter (New Developments in Functional Lipids (Kinousei Shishitsuno Shintennkai), Osamu Suzuki, 2001).

As another useful physiological effect, there can be mentioned an anti-allergy effect (The European Respiratory Journal, Nagatsuka T. 2000, 16: 861; The Journal of Infectious Diseases, McMurray D N, 2000, 182: 861), and one of the mechanisms thereof is proposed to be an effect on the function of immunocompetent cells. As one of the studies that support this, as shown in Japanese Unexamined Patent Publication (Kokai) No. 10-1434 to Yazawa et al., the effect of EPA and DHA on eosinophil migration has been investigated, and revealed that the intraperitoneal administration of 100 mg of EPA ethylester or 50 mg of DHA ethylester can inhibit eosinophil migration in the delayed type allergy in guinea pigs.

However, this experiment is a confirmation of a biological reaction when EPA and DHA were intraperitoneally administered, and cannot be considered to be an experiment that simulates a situation in which they were actually ingested as a foodstuff. When intraperitoneal administration and oral administration are compared, it can be easily conjectured that the concentrations of EPA and DHA are overwhelming higher in the abdominal cavity, in which eosinophils can infiltrate, in the former, i.e. the physiological activity can be more easily detected. Thus, it is unknown whether oral ingestion provides such effects or not.

There are also problems of parts being easily oxidized and offensive odors resulting from the structural characteristics of EPA and DHA. EPA and DHA have unsaturated bonds in their molecules, or parts that are easily oxidized: five in EPA and six in DHA. By undergoing oxidation, there is quality deterioration, and the possibility cannot be ruled out that not only does it impair the physiological functions described above, but the oxidation products formed may be detrimental to a living body. Furthermore, these oxidation products of PUFAs are known to emit exceptionally bad orders, and become worse with accelerated oxidation over time.

As a countermeasure against easily oxidized EPA and DHA, antioxidants, deodorants, masking agents, etc., have been contrived. However, because of various problems in that their efficacy for preventing oxidation and that its duration are not satisfactory and some additives may cloud the appearance, none are considered effective preventive measures (Japanese Unexamined Patent Publication (Kokai) No. 2-55785, Japanese Unexamined Patent Publication (Kokai) No. 3-100093, Japanese Unexamined Patent Publication (Kokai) No. 2004-137420). Despite the useful biological activity of EPA and DHA, it is difficult to stably maintain their quality even with a variety of measures, which represents one of the reasons that limit the range of application into foodstuffs.

From the foregoing, food materials that are medically useful and that are excellent in safety and quality stability are being sought after.

In recent years, because of changes in the environment and eating habits, genetic factors and the like, the number of patients afflicted with allergic diseases has increased. Pathological conditions of allergic diseases are roughly divided into type I to type IV based on the mechanism of pathogenesis and the related functional molecules. Mast cells are considered to be closely related to type a I allergy, also termed as delayed type allergy, among them. In a type I allergy, when a living body is exposed to a certain antigen, an antigen-specific IgE antibody is produced by B cells via antigen presenting cells and helper T cells.

Subsequently, IgE antibody binds to the surface of mast cells to enter into the state of a guard against the reentry of antigen. Mast cells in this state capture antigen that enter the surface of the membrane, and initiate degranulation so as to release various chemical mediators such as histamine and leukotrienes. The subsequent binding of these chemical mediators to the receptors causes so-called "allergic reactions" i.e. physiological phenomena that are detrimental to humans such as edema, reddening, itching, airway resistance and enhanced mucous secretion.

Under these circumstances, various attempts for alleviating allergic reactions have been made, by inhibiting the function of mast cells, specifically by a method of suppressing the degranulation of mast cells to suppress the release of chemical mediators, a method of suppressing the synthesis of chemical mediators, or a method of inhibiting the binding of the released chemical mediators and receptors, specifically by suppressing the actions of chemical mediators produced by mast cells. It is recognized now that many of the pharmaceutical agents used for alleviating itching associated with atopic dermatitis, and treating pollinosis, allergic conjunctivits etc., are based on any of the mechanisms described above (Internet HP "The Rheumatism & Allergy Information Center", Maki Hasegawa, 2005 Apr. 4, Allergic inflammatory diseases—New approaches, Motohiro Kurosawa, 1994).

However, some reports describe that not only the function of the above chemical mediators produced by mast cells, but the number per se of mast cells identified in the lesion are changed. For example, it has been found that the differentiation and proliferation of mast cells in the nasal mucosa of patients with allergic rhinitis are more frequent than those with nonallergic diseases (Journal of the Oto-Rhino-Laryngological Society of Japan (Nippon Jibiinkoka Gakkai Kaiho), Naoshi Yoshida, 2001, 104: 504). It has also been revealed that patients who have asthma, the number of mast cells localized in bronchial smooth muscles are significantly greater than normal healthy subjects (Current Opinion in Allergy and Clinical Immunology, Peter B, 2003, 3: 45).

There are similar reports on skin diseases, for example increases in mast cells have been reported in lesions, etc., of basal cell carcinoma, psoriasis vulgaris and atopic dermatitis (Allergy, Shoso Yamamoto, 2000, 49: 455). In other words, as a means for suppressing and/or alleviating diseases closely related to enhanced mast cell count, it is important not only to control the amount and function of chemical mediators produced by inflammatory cells, specifically mast cells, but also to suppress the abnormal growth of the mast cells per se to keep the number of these cells at normal levels, and it is believed that by controlling the processes, more effective and multi-faceted prevention and treatment of diseases can be attained.

For example, it has been found that steroid external preparations, immunosuppressive external preparations or the like of which clinical significance has been recognized against allergic dermatitis, etc., not only exhibit significant improvement in the dermatitis symptom score associated with dermatitis, but also significantly suppress increases in the number of mast cells in the lesions of dermatitis in the NC/Nga mice which is an animal model of allergic dermatitis (Japanese Journal of Pharmacology, Hiroi J, 1998, 76: 175). This also strongly suggests that the therapeutic effect and mast cell count are correlated, and supports the importance of regulating mast cell count at an appropriate level.

Thus, these pharmaceutical drugs have been demonstrated to be useful in the prevention and/or treatment of various mast cell-related diseases such as allergic diseases, whereas they have problems in safety and methods of use. Steroid external preparations have side effects, such as blushing, atrophy of the skin, and a rebound phenomenon in which suspending administration may aggravate dermatitis, whereas immunosuppressive external preparations have problems in that their use may facilitate skin tumors and their efficacy is greatly affected by the application site and the state of the barrier function of the skin (Journal of the Japanese Dermatological Association, Masutaka Furue, 2004, 114: 135).

Under these circumstances, materials have long been sought that are medically useful, that can be used safely by everyone, and that can effectively suppress enhancement in the number of mast cells.

Patent document 1: Japanese Patent No. 3354581
Patent document 2: Japanese Unexamined Patent Publication (Kokai) No. 8-3036
Patent document 3: Japanese Unexamined Patent Publication (Kokai) No. 2-55785
Patent document 4: Japanese Unexamined Patent Publication (Kokai) No. 3-100093
Patent document 5: Japanese Unexamined Patent Publication (Kokai) No. 2004-137420
Nonpatent document 1: Cosmetic & Toiletries, Nissen H P, 1995, 119: 71
Nonpatent document 2: Diabetic Medicine, Jamal G A, 1990, 7: 319
Nonpatent document 3: Arthritis Rhermatism, Zurier R B, 1996, 39: 1808
Nonpatent document 4: British Medical Journal, Kernoff P B A, 1977, 2: 1441
Nonpatent document 5: Lipids, Taki H., 1993, 28: 873
Nonpatent document 6: Lipids, Cedric H., 1984, 19: 699
Nonpatent document 7: Immunology, Maaike M B W D, 2003, 110: 348
Nonpatent document 8: The Journal of Immunology, Deniela S, 1989, 143: 1303
Nonpatent document 9: Archives of Dermatological Research, Iversen L, 1992, 284: 222
Nonpatent document 10: Prostaglandin Leukotrienes and Essential Fatty Acids, Zurier R B, 1999, 60: 371
Nonpatent document 11: American Journal of Clinical Nutrition, Harrobin D F, 2000, 71: 367
Nonpatent document 12: Prostaglandins Leukotrienes and Medicine, Mauku M S, 1982, 9: 615
Nonpatent document 13: The Lancet, Wright S, 1982, 20: 1120
Nonpatent document 14: Abstract of the 50th General Meeting of the Japanese Society of Allergology, Zui Hamada, 2000, pp. 999
Nonpatent document 15: Prostaglandins Leukotrienes and Essential Fatty Acids, Navarette R, 1992, 46: 139
Nonpatent document 16: British Journal of Dermatology, Henz B M, 1999, 140: 685
Nonpatent document 17: Abstract of the 58th meeting of the Japanese Society of Nutrition and Food Science, Chika Horikawa, 2004, pp. 219
Nonpatent document 18: New Developments in Functional Lipids (Kinosei Shishitsuno Shintennkai), Osamu Suzuki, 2001
Nonpatent document 19: γ-Linolenic Acid, Recent Advances in Biotechnology and Clinical Applications, Hundy Y S, 2001
Nonpatent document 20: American Journal of Clinical Dermatology, Chari S, 2001, 2: 1
Nonpatent document 21: Paediatric Respiratory Reviews, McMillan R M, 2001, 2: 238
Nonpatent document 22: Agents Actions, Rask-Madsen J, 1992, C37 (Japanese Unexamined Patent Publication (Kokai) No. 8-3036)
Nonpatent document 23: Japanese Journal of Pharmacology, Hiroi J, 1998, 76: 175
Nonpatent document 24: American Journal of Respiratory and Critical Care Medicine, Wenzel S E, 1995, 152: 897
Nonpatent document 25: Journal of the Japanese Dermatological Association, Masutaka Furue, 2004, 114: 135
Nonpatent document 26: ZYFLO™ FLIMTAB, the package insert, Abbott Laboratories, 1998
Nonpatent document 27: The European Respiratory Journal, Nagatsuka T. 2000, 16; 861
Nonpatent document 28: The Journal of Infectious Diseases, McMurray D N, 2000, 182: 861
Nonpatent document 29: British Medical Journal, Kernoff P B A, 1977, 2: 1441
Nonpatent document 30: The Journal of Immunology, Deniela S, 1989, 143: 1303
Nonpatent document 31: Archives of Dermatological Research, Iverson L, 1992, 284: 222
Nonpatent document 32: Maki Hasegawa, 2005 Apr. 4, Allergic inflammatory diseases—New approaches, Motohiro Kurosawa, 199
Nonpatent document 33: Journal of the Oto-Rhino-Laryngological Society of Japan (Nippon Jibiinkoka Gakkai Kaiho), Naoshi Yoshida, 2001, 104: 504
Nonpatent document 34: Current Opinion in Allergy and Clinical Immunology, Peter B, 2003, 3: 45
Nonpatent document 35: Prostaglandins Leukotrienes and Essential Fatty Acids, Gueck T. 2003, 68: 317
Nonpatent document 36: Veterinary Dermatology, Gueck T. 2004, 15: 309
Nonpatent document 37: Allergy, Shoso Yamamoto, 2004, 49: 45.

DISCLOSURE OF THE INVENTION

It is an object of the present invention to provide an amount of DGLA suitable for more safely and effectively prevent and treat atopic dermatitis.

We have found that PUFAs and their related metabolites become quantitatively and qualitatively aberrant due to various factors, which in turn causes undesirable biological changes, or conversely as a result of undesirable biological changes, PUFAs and their related metabolites often become quantitatively and qualitatively aberrant, and under these conditions, the basic principle is to correct the aberrant states by positively ingesting PUFAs, and in particular, the n6-series PUFAs among the PUFAs are extremely useful, and work well at doses smaller than GLA, and thereby have completed the present invention.

Thus, the present invention provides a composition which comprises DGLA and which has the effect of preventing or treating skin diseases.

The composition is, for example, a food composition or a pharmaceutical composition.

Dermatitis is, for example, allergic dermatitis or atopic dermatitis.

The content of DGLA in the composition is, for example, an ingestable amount of 5 mg-600 mg of DGLA per adult per day. For example, the amount of DGLA can be ingested at 5 mg-200 mg or 5 mg-150 mg of DGLA per adult per day.

DGLA may be present in the form of a glyceride, a phospholipid, a glycolipid, an alkylester, or a free fatty acid. The glyceride may be, for example, a triglyceride, a diglyceride, or a monoglyceride. Preferably said glyceride is a triglyceride and/or a diglyceride.

The composition may be in the form of, for example, a pill, a tablet or a capsule.

The composition of the present invention comprises DGLA and can take a form of a food or beverage indicated for the effect of preventing or treating skin diseases. For example, it can be a food or beverage indicated for the effect of preventing or treating skin diseases, said food or beverage comprising an amount suitable to ingest 5 mg-600 mg of DGLA per adult per day. Furthermore, it can be a food or beverage indicated for the effect of preventing or treating skin diseases, said food or beverage comprising an amount suitable to ingest 5 mg-200 mg of DGLA per adult per day, or a food or beverage indicated for the effect of preventing or treating skin diseases said food or beverage comprising an amount suitable to ingest 5 mg-150 mg of DGLA per adult per day.

It is another object of the present invention to provide a food or pharmaceutical composition that is safer and more effective for the prevention or treatment of various diseases closely related to eosinophil infiltration and increased cell count.

After intensive and extensive research in order to resolve the above problems, the present inventors have found that dihomo-γ-linolenic acid (DGLA) is very useful in inhibiting eosinophil infiltration, and can more effectively inhibit than other PUFAs, and thus have completed the present invention.

The present invention provides a composition which comprises DGLA and which has the effect of preventing or treating various diseases closely related to eosinophil infiltration and increased cell count.

The composition is a food composition or a pharmaceutical composition.

The above diseases are skin diseases, such as atopic dermatitis, eczema and psoriasis, respiratory system diseases, such as bronchial asthma, chronic obstructive pulmonary disease (COPD), hypersensitivity pneumonitis and eosinophilic pneumonia, and digestive system diseases, such as eosinophilic gastroenteritis and ulcerative colitis.

EPA and DHA are termed as the n-3 series PUFA as shown in FIG. 2, whereas DGLA belongs to the n-6 series PUFA based on the synthetic pathway in the body. DGLA is a highly safe food ingredient found in meat, eggs, seafoods etc., but the content has been found to be much lower than EPA or DHA or arachidonic acid of the same n-6 series PUFAs. As shown in Japanese Patent No. 3354581, the present inventors have invented a fermentation method for producing DGLA lipids by a microbial strain, thus enabling mass production of a triglyceride SUNTGD in which about 40% of the constituent fatty acids are DGLA. Structurally speaking, DGLA has three unsaturated bonds which are smaller than EPA or DHA, and this ingredient is refractory to oxidation thus emitting no orders and having excellent stability.

Regarding the physiological function of this ingredient, part of it has been confirmed in vivo or in vitro: in vivo, effects of inhibiting platelet agglutination (British Medical Journal, Kernoff P B A, 1977, 2: 1441), delayed-type footpad edema (Lipids, Taki H., 1993, 28: 873), blood pressure increase (Lipids, Cedric H., 1984, 19: 699) and other effects have been reported, and in vitro, effects of inhibiting the production of cytokines, such as interleukin-2, -10 and tumor necrosis factor (TNF-α) (Immunology, Maaike M B W D, 2003, 110: 348; The Journal of Immunology, Deniela S, 1989, 143: 1303), leukotriene production (Archives of Dermatological Research, Iversen L, 1992, 284: 222), and T cell growth (Prostaglandin Leukotrienes and Essential Fatty Acids, Zurier R B, 1999, 60: 371) and other effects have been reported.

However, no direct demonstration of the effect on eosinophils has been made. As described above, though DGLA is expected to be safe and be stabile, nothing is known on the physiological function thereof, specifically whether it has any effect on eosinophils, or the intensity of the effect, if any, compared to PUFAs.

DGLA may be present in the form of a glyceride, a phospholipid, a glycolipid, an alkylester, or a free fatty acid. Said glyceride may be, for example, a triglyceride, a diglyceride, or a monoglyceride. Preferably said glyceride is a triglyceride and/or a diglyceride.

The composition may be in the form of, for example, a pill, a tablet or a capsule.

The composition of the present invention comprises DGLA and can be included in a food or beverage for preventing or treating various diseases that are closely related to eosinophil infiltration and increased cell count. For example, it can be a food or beverage for preventing or treating various diseases that are closely related to eosinophil infiltration and increased cell count.

It is a further object of the present invention to provide a safer and more effective food or a pharmaceutical composition for various diseases that are closely related to increased mast cell count.

After intensive and extensive research in order to resolve the above problems, the present inventors have found that dihomo-γ-linolenic acid (DGLA) is very useful in inhibiting enhancement in a number of mast cells, and thus have completed the present invention.

Considering medically or nutritionally useful food ingredients, there can be mentioned dihomo-γ-linolenic acid (DGLA), a n-6 series polyunsaturated fatty acid (PUFA) as shown in FIG. 2, as one of the candidate materials. DGLA is abundantly found in meat, eggs, seafood and the like, which have been ingested by mankind for a long period of time and are naturally very safe. However, the content has been found to be much lower than arachidonic acid of the same n-6 series PUFAs or EPA or DHA. As shown in Japanese Patent No. 3354581, the present inventors have invented a fermentation method for producing DGLA lipids by a microbial strain, thus enabling mass production of a triglyceride SUNTGD in which about 40% of the constituent fatty acids are DGLA.

Regarding the physiological function of this ingredient, part of it has been confirmed in vivo or in vitro: in vivo, effects of inhibiting platelet agglutination (British Medical Journal, Kernoff P B A, 1977, 2: 1441), delayed-type footpad edema (Lipids, Taki H., 1993, 28: 873), blood pressure increase (Lipids, Cedric H., 1984, 19: 699) and other effects have been reported, and in vitro, effects of inhibiting the production of cytokines such as interleukin-2, -10 and tumor necrosis factor (TNF-α) (Immunology, Maaike M B W D, 2003, 110: 348; The Journal of Immunology, Deniela S, 1989, 143: 1303), leukotriene production (Archives of Dermatological Research, Iversen L, 1992, 284: 222), and T cell growth (Prostaglandin Leukotrienes and Essential Fatty Acids, Zurier R B, 1999, 60: 371) and other effects have been reported. However, no direct demonstration of the effect on eosinophils has been made.

On the other hand, linoleic acid (LA) and γ-linolenic acid (GLA) among the same n-6 series PUFAs, effects on mast cells have been investigated, and the former has been reported to enhance the release of stimulation-responsive histamine from lined mast cells (Prostaglandin Leukotrienes and Essential Fatty Acids, Gueck T. 2003, 68: 317). The latter has been found to inhibit histamine release in the same test system (Veterinary Dermatology, Gueck T. 2004, 15: 309). However, both studies examined the effect on the release of chemical mediators from mast cells, however, their effect on the number of mast cells is not known.

As described above, it was not known what effects DGLA might have on the number of mast cells.

Thus, the present invention provides a composition which comprises DGLA and which prevents or treats various diseases closely related to increased cell count.

The composition is a food composition or a pharmaceutical composition.

The above diseases are skin diseases, such as atopic dermatitis, eczema and psoriasis, basal cell carcinoma, and prickle cells, bronchial asthma, pollinosis, allergic rhinitis, allergic conjunctivitis and the like.

DGLA may be present in the form of a glyceride, a phospholipid, a glycolipid, an alkylester, or a free fatty acid. The glyceride may be, for example, a triglyceride, a diglyceride, or a monoglyceride. Preferably the glyceride is a triglyceride and/or a diglyceride.

The composition may be in the form of, for example, a pill, a tablet or a capsule.

The composition of the present invention comprises DGLA and can take a form of a food or beverage indicated for the effect of preventing or treating various diseases that are closely related to increased mast cell counts. For example, it can be a food or beverage indicated for the effect of preventing or treating various diseases that are closely related to increased mast cell counts.

BEST MODE FOR CARRYING OUT THE INVENTION

Figure 1:
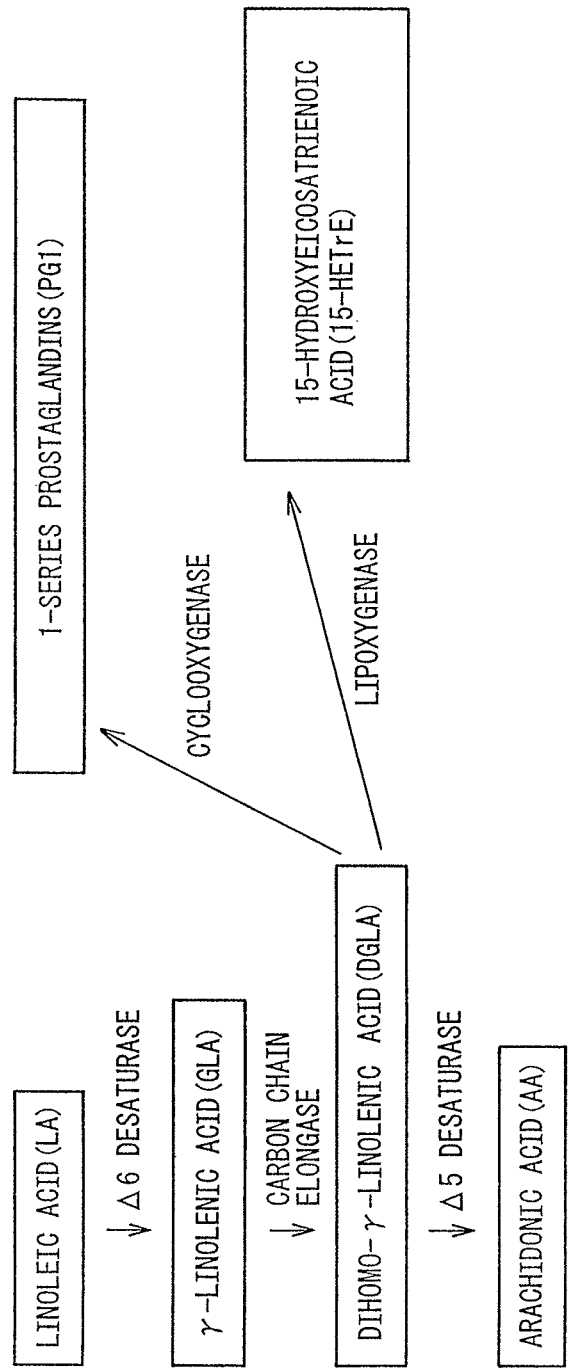
FIG. 1 is a drawing showing the metabolic pathway of n-6 series polyunsaturated fatty acids (PUFAs).
Figure 2:
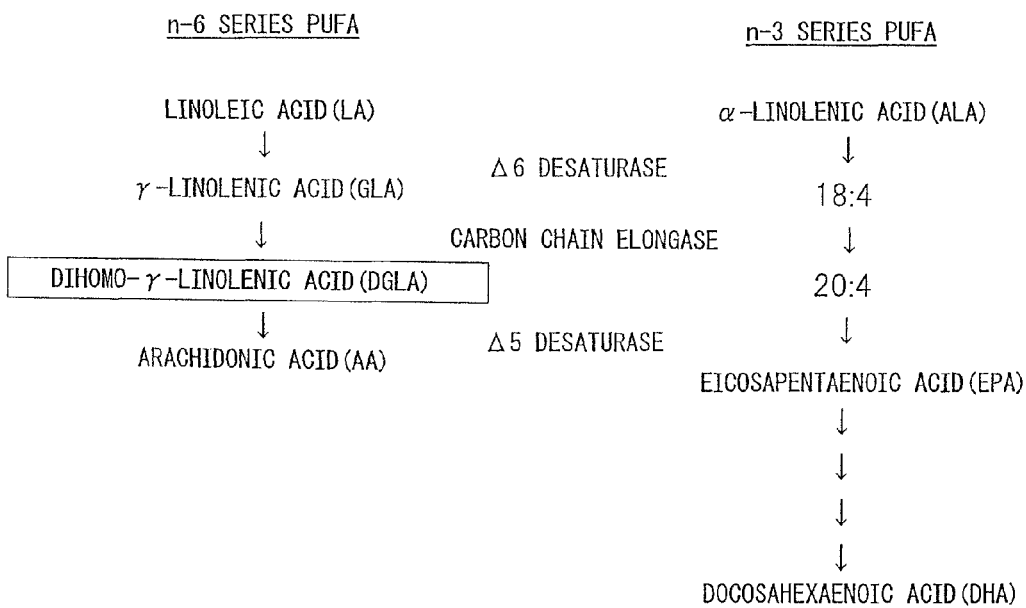
FIG. 2 shows the metabolic pathways of n-6 series and n-3 series polyunsaturated fatty acids.

The present invention will now be explained in detail below.

As food compositions, there can be mentioned food supplements and (medical) prescribed products and preparations such as tablets, pills and capsules. Furthermore, there can be mentioned solid or liquid foodstuffs, for example dairy products (margarine, butter, milk, yogurt), bread, cake; drinks, for example beverages (tea, coffee, cocoa, chocolate drinks), fruit juice, soft drinks (for example carbonated drinks); confectioneries; oily foods (snacks, salad dressings, mayonnaise), soup, sauce, carbohydrate-rich foods (rice, noodles, pasta), fish-containing foods, baby food (for example, baby formula, as a liquid or a powder), pet food, and prepared foods or microwavable food.

DGLA may be derived from any suitable source. However, there are few known natural lipid sources having a high DGLA content, and minute amounts may be extracted from cow's liver, a pig's kidney, egg-yolk, etc. With the progress in the microbial fermentation technology in recent years, it may be derived from microorganisms, for example fungi, bacteria or yeast.

Suitable fungi belong to the order of Mucorales, for example *Mortierella, Pythium* or *Entomophyhora*. A suitable source of DGLA is *Mortierella*. More preferably it is derived from *Mortierella alpina*. As a DGLA-containing lipid, a triglyceride in which about 40% of the constituent fatty acids are DGLA may be prepared by a microbial fermentation method using *Mortierella*.

In addition to DGLA, one or more additive PUFAs may be supplied. In addition to DGLA, it may be another n-6 series PUFA (for example linoleic acid (LA)), γ-linolenic acid (GLA) and arachidonic acid (AA)) or a n-3 series PUFA (for example EPA, DHA).

As a physiologically acceptable derivative of this acid that can be converted to DGLA for use in the present invention, there can be mentioned the form of a DGLA-containing triglyceride, diglyceride, and monoglyceride, or a phospholipid, a glycolipid, a free fatty acid, a fatty acid ester (for example, methyl or ethyl ester), and a sterol ester.

Preferably, PUPA is present in an oil. This can be a pure oil, a processed oil (for example, a chemically and/or enzymatically processed oil), or a concentrated oil. Though these oils may contain 10-100% of PUFAs, the content of the desired PUFA, for example DGLA, may be 5% or more if the oil is derived from a microorganism, preferably 10% or more, more preferably 25% or more. The oil may contain one or more PUFAs within the concentration range of the above percentage. The oil may be a single oil derived from a single cell or a microorganism, or may be a blended or mixed oil of two or more oils derived from different sources. The oil may contain one or more additives, for example an antioxidant (for example, tocopherol, vitamin E, tocotrienol, an ascorbic acid derivative, a palmitate or an ester, astaxanthin), sesamine, CoQ10 or the like.

The present invention may be used to enhance the PUFA level of a normal healthy individual who has had a sufficient meal or an individual who shows a normal PUFA level for the purpose of preventing diseases, and maintaining health.

However, it can also be used for individuals whose PUFA levels are low or insufficient. For example, it can be used for prophylaxis, prevention, improvement and treatment of diseases or conditions related to abnormal or low levels of n-3 series or n-6 series PUFAs in blood. Thus, the present invention provides application in subjects who have low DGLA levels, for example subjects who cannot convert and/or effectively convert LA to GLA and DGLA or GLA to DGLA. Thus, in appropriate patients, Δ6-desaturase and/or carbon chain elongase may be dysfunctional, insufficient or deficient.

The present invention specifically provides the use in humans having low levels of DGLA; for example when an immunological level of atopic dermatitis, is low, immunological level is decreased or enhanced, and the present invention provides the use to such subjects at an abnormal immunological state.

It can also be used to correct states in which DGLA levels are low or DGLA levels are not normal, and other states, for example various skin diseases such as dermatitis, eczema and UV-derived skin disorders, rheumatoid arthritis, diabetes mellitus, alcoholics and smokers.

Specifically the present invention provides the use in subjects with various diseases closely related to eosinophil infiltration and increased cell count, such as skin diseases, respiratory system diseases and digestive system diseases.

Skin diseases may indicate atopic dermatitis, eczema and psoriasis, respiratory system diseases may indicate bronchial asthma, chronic obstructive pulmonary disease (COPD), hypersensitivity pneumonitis and eosinophilic pneumonia, and digestive system diseases may indicate eosinophilic gastroenteritis and ulcerative colitis.

Specifically the present invention provides the use in subjects with various diseases in which increased mast cell count has been observed, and may indicate skin diseases, such as atopic dermatitis, eczema, psoriasis, basal cell carcinoma and prickle cell carcinoma, bronchial asthma, pollinosis, allergic rhinitis, allergic conjunctivitis and the like.

EXAMPLES

The present invention will now be explained more specifically below.

Example 1

As described above, since it was proposed that ingestion of DGLA is useful for the prevention or treatment of atopic dermatitis, its usefulness in experimental animals was investigated using a triglyceride SUNTGD, a DGLA lipid having DGLA as the main constituent fatty acid, that was prepared according to the method described in Japanese Patent No. 3354581. As an animal model of atopic dermatitis, NC/Nga mice were used in this study. Since mice have been recognized as one of the most useful models of atopic dermatitis at present, and steroid external preparations and immunosuppressive external preparations currently used in the clinical setting for the treatment of atopic dermatitis have also been demonstrated to be effective in mice it has widely been used in screening of therapeutic agents for atopic dermatitis.

In a conventional feeding environment, mice are known to spontaneously develop dermatitis at about 8 weeks after birth, and then the inflammation aggravates to a chronic type with the passage of days, and develop human atopic dermatitis-like symptoms both macroscopically and histopathologically. As characteristics of this pathological condition, there can be mentioned increased serum IgE accompanied by the onset of dermatitis and marked infiltration of immunocompetent cells, such as mast cells, eosinophils and T cells at the lesion.

In this study, male or female NC/Nga mice were prepared and three groups of seven mice per group were used in a conventional feeding environment. The following three types of diets shown in FIG. 1 were prepared, and were fed ad libitum at post-ablactation week 5 and until the completion of the study at week 12. The groups comprised a control diet group, a high DGLA diet group and a low DGLA diet group SUNTGD was added to the diet of the latter two groups, at about 1.0% DGLA (calculated as the amount of free fatty acids), for the high DGLA group, and at about 0.5% DGLA (calculated as the amount of free fatty acids) for the low DGLA group. Since the mean body weight of the mice was 20 g and the mean daily diet ingestion was about 2 g, the amount ingested of DGLA in this experiment was estimated to be about 1000 mg/kg per day for the high DGLA group, and about 500 mg/kg per day for the low DGLA group. The amount of total fatty acids in the diet was adjusted to be 5% for all of the groups. The items evaluated were the macroscopic score of dermatitis symptoms under a blinded condition, scratching behavior and plasma IgE.

As a result, without exhibiting any aberration in body weight both of the DGLA diet groups exhibited a statistically significant inhibitory effect in all of the evaluation items of the macroscopic score of dermatitis symptoms (Table 2), scratching behavior (Table 3), amount of plasma IgE produced (Table 4), suggesting the possibility that the ingestion of DGLA may be useful for the prevention of atopy. The fatty acid composition (Table 5) in the plasma at this time reflected the effect of the diet, and in all of the organs, increases in the amount of DGLA and decreases in the amount of LA were noted, dependent on the dose of the DGLA diet, with the variation in fatty acid composition being most conspicuous in the spleen, suggesting that DGLA may have a great impact on the physiological function of the immune system. More surprisingly, the preventive effect was independent of the dose of DGLA, i.e. the effect of preventing atopy tended to be more prominent in the low DGLA diet group compared to the high DGLA diet group.

As described above, the fatty acid composition in the living body exhibited a dose dependent increase in DGLA, it is obviously not the attenuation of the effect by inhibiting the absorption of DGLA per se etc. This strongly suggests the possibility that there may be an optimum amount of DGLA for preventing atopy in mice or humans, i.e. an amount lower than that of the low DGLA diet used in this study may exhibit the highest inhibitory effect. Furthermore, in the case of variation in the amount of DGLA in the plasma by the DGLA diet, DGLA in plasma phospholipids was 4.3% in the low DGLA diet group, which was specifically effective in the improvement of atopic dermatitis-like symptoms, and in the control diet group it was 1.0%, which indicates about 4-fold or 3% by weight increase revealing that such an enhancement in the amount of plasma DGLA is one of the parameters that most contribute to the therapeutic effect of atopic dermatitis.

If the ingestion of DGLA could promote such a correction in the amount of DGLA in humans, atopic dermatitis is expected to be improved. For the mice model, as described above, GLA has been reported (Abstract of the 50th General Meeting of the Japanese Society of Allergology, Zui Hamada, 2000, pp. 999), and the dose therein was about 1250 mg/kg per day, whereas the amount of the low DGLA diet used was about 500 mg/kg per day or less. From this fact as well, it may be expected that DGLA can prevent atopic dermatitis more efficiently than GLA. Furthermore, ALA, a n-3 series PUFA, has been investigated in the same model (Prostaglandin Leukotrienes and Essential Fatty Acids, Suzuki R, 2002, 66: 43) wherein, although the exact dose is not known, no effect of preventing atopic dermatitis, such as the correction of dermatitis symptoms and blood IgE can be recognized even though ALA in the erythrocyte membrane in the living body becomes markedly increased in a diet containing a large amount of ALA.

TABLE 1

Table of ingredients in each diet (unit: %)

| Ingredient (%) | Control diet | High DGLA diet | Low DGLA diet |
| --- | --- | --- | --- |
| Casein | 20.0 | 20.0 | 20.0 |
| DL-methionine | 0.3 | 0.3 | 0.3 |
| Cornstarch | 45.0 | 45.0 | 45.0 |
| Pregelatinized cornstarch | 10.0 | 10.0 | 10.0 |
| Sucrose | 10.0 | 10.0 | 10.0 |
| Cellulose powder | 5.0 | 5.0 | 5.0 |
| AIN76 mineral mix | 3.5 | 3.5 | 3.5 |
| AIN76 vitamin blend | 1.0 | 1.0 | 1.0 |
| Choline bitartarate | 0.2 | 0.2 | 0.2 |
| Corn oil | 3.34 | 0.84 | 2.09 |
| Lard oil | 1.67 | 0.42 | 1.04 |
| SUNTGD(*1) | 0.00 | (*2)2.50 | (*3)1.25 |
| Olive oil | 0.00 | 1.25 | 0.63 |
| Total | 100.0 | 100.0 | 100.0 |

(*1)A triglyceride in which about 40% of the constituent fatty acids are DGLA
(*2)Corresponds to about 1.0% in the diet as the amount of free DGLA
(*3)Corresponds to about 0.5% in the diet as the amount of free DGLA

TABLE 2

Scores of dermatitis symptoms of NC/Nga mice (mean ± standard deviation, N = 7)

| | At 10-week-old | At 12-week-old |
| --- | --- | --- |
| Control diet group | 7.1 ± 0.5 | 9.1 ± 1.0 |
| High DGLA diet group | *2.1 ± 1.0 | *3.0 ± 0.5 |
| Low DGLA diet group | *1.4 ± 0.3 | *1.6 ± 0.4 |

*p < 0.05 (Dunnett's test vs. the control group)

TABLE 3

Scratching behavior in NC/Nga mice (the number of scratching per 20 minutes, mean ± standard deviation, N = 7)

| | At 10-week-old | At 12-week-old |
| --- | --- | --- |
| Control diet group | 75.9 ± 10.7 | 51.7 ± 9.1 |
| High DGLA diet group | *18.0 ± 8.9 | 35.0 ± 7.1 |
| Low DGLA diet group | *21.4 ± 6.7 | **21.9 ± 5.7 |

*p < 0.05,
**p < 0.01 (Student t-test vs. the control group)

TABLE 4

Total plasma IgE in 12-week-old NC/Nga mice (μg/ml, mean ± standard deviation, N = 7)

| | At 12-week-old |
| --- | --- |
| Control diet group | 64.2 ± 39.8 |
| High DGLA diet group | 29.8 ± 21.0 |
| Low DGLA diet group | **15.6 ± 3.6 |

*p < 0.01 (Dunnett's test vs. the control group)

TABLE 5

Phospholipid fatty acid composition in the plasma of 12-week-old NC/Nga mice (% of phospholipid in the total fatty acids, mean ± standard deviation, N = 7)

| Fatty acid | Control diet | High DGLA diet | Low DGLA diet |
| --- | --- | --- | --- |
| LA | 15.4 ± 4.1 | **5.6 ± 2.0 | **8.4 ± 2.6 |
| 20:0/18:3G | 0.0 ± 0.1 | 0.1 ± 0.1 | 0.0 ± 0.0 |
| DGLA | 1.0 ± 0.4 | **7.6 ± 4.0 | **4.3 ± 1.5 |
| AA | 10.3 ± 2.0 | **15.7 ± 3.7 | **16.5 ± 1.6 |
| EPA | 0.0 ± 0.0 | 0.0 ± 0.0 | 0.0 ± 0.0 |
| DHA | 2.2 ± 0.8 | 2.3 ± 0.4 | 1.8 ± 0.6 |

**p < 0.01 (Student t-test vs. the control group)

Example 2

In order to clarify the relationship between the amount of DGLA orally ingested in humans and the internal DGLA level, the amount of DGLA orally ingested was investigated by examination of the diet, and after drawing blood, the amount of DGLA in the serum phospholipids was determined. The subjects were eleven healthy males aged 60-70, and were asked to keep a diary of the content of their diets. From the diary, the amount ingested by each food material was determined for meat, eggs, and seafood known to contain DGLA, and using the DGLA content of each food material calculated from "Fourth revised STANDARD TABLES OF FOOD COMPOSITION IN JAPAN, Standard Tables of Dietary Lipids in Japan (1990)", the amount ingested of DGLA per day per person was calculated. From the amount of DGLA ingested per week, the mean amount of DGLA ingested per day was calculated for each person.

On the other hand, blood was drawn the day after the last entry of the diary, and for the serum phospholipid fractions obtained, the fatty acid composition was analyzed according to a standard method. Thus, from the serum the lipid component extracted by the Folch method, a standard method, and the lipid was fractionated on a thin layer chromatography (the developing solution is hexane/diethyl ether=7/3) to obtain the phospholipid fraction. The silica gel layer was directly scraped, and was reacted in hydrochloric acid-methanol at 50° C. for 3 hours, followed by extraction with hexane to obtain a fatty acid methyl ester mixture. As the internal standard, pentadecanoic acid was used. The fatty acid methyl ester mixture was analyzed by a capillary gas chromatography to obtain DGLA (% by weight) in the total fatty acids in the serum phospholipid.

The result demonstrated that there is a positive correlation between the mean daily amount ingested of DGLA and DGLA (% by weight) in the serum phospholipid. When X=the mean daily amount (mg) ingested of DGLA and Y=DGLA (% by weight) in the serum phospholipid, the correlation linear equation becomes Y=0.0312 X+1.361, indicating a relationship that with each increase of about 32 mg in the amount of DGLA ingested, DGLA in the serum phospholipid increases by 1% by weight. Further known from this result is the tendency that the changes in blood DGLA after oral ingestion of DGLA are more pronounced in humans than in mice. In the earlier result on mice, it was established that, for the low DGLA diet group, by ingesting 500 mg/kg of DGLA in terms of body weight for substantially 8 weeks, the amount of DGLA in the plasma phospholipid increases 3% by weight.

In the study on humans, when the body weight is 60 kg, by calculating that by ingestion of 32 mg/60 kg=0.53 mg/kg of DGLA, the amount of DGLA in the serum phospholipid increases 1% by weight. Also, when DGLA in the plasma phospholipid increased about 3% by weight in mice, the symptoms of atopic dermatitis were effectively improved, and conversely in humans, the amount of DGLA required to increase the amount of DGLA in serum phospholipid about 3% by weight, may be about 100 mg per day. Further the amount of orally ingested GLA that can improve atopic dermatitis in humans is about 180-1440 mg per day, and is strongly suggested that smaller amounts of DGLA can improve atopy.

Example 3

For some skin diseases, it is known that the skin may be damaged by sunlight. Specifically, ultraviolet light classified as UV-B at wavelengths of 290-320 nm is considered a major factor responsible for acute sunburn of the skin, pigmentation, suntan, skin cancer and the like. In order to explore the further possibility of DGLA affecting skin function, the effect of DGLA on acute inflammation of the skin was evaluated using an UV-B-induced acute inflammation guinea pig model. This model animal is one model widely used for drug screening in the development of pharmaceutical agents intended for anti-inflammatory effects.

In this study, male Hartley guinea pigs were prepared and divided into a control diet group and a DGLA diet group. Each diet group was continued to be given ad libitum for three weeks, from 5 week-old to 7 week-old animals, at the completion of the experiment. The DGLA diet used this time is different from the composition of the mouse diet described earlier and was adjusted to about 0.08% of DGLA (calculated as the free fatty acid) in the diet. Thus, since the mean body weight of the guinea pigs was about 400 g and the mean daily amount ingested was about 30 g, the amount ingested of DGLA in this experiment was estimated to be about 60 mg/kg per day. After three weeks of free access to the diet, the back of the guinea pig was shaved, and after fixing the animals on an abdominal position, they were irradiated using a UV irradiator (Dermaray™, type M-DMR-I, Eisai) and a UV-B tube (FL-20S-E-30 lamp, central wavelength 305 nm, Toshiba) at a distance of 5 cm from the tube for 15 minutes to induce an acute inflammatory reaction. After the induction of skin erythema reaction, it was scored under a blind condition according to the Draize method.

The result as shown in Table 6 indicated that the DGLA diet group exhibited a tendency to inhibit an acute skin inflammatory reaction resulting from UV-B, specifically a statistically significant inhibitory effect at one hour after exposure to UV-B. At this time it was confirmed (though the result is not shown) that the amount of DGLA in the phospholipid of the plasma, the skin and other organs significantly increases in the DGLA diet group compared to the control diet group. Based on the above result, it was found that a DGLA diet is useful in the prevention of UV-induced skin damage.

TABLE 6

Skin erythema score in UV-B-induced acute inflammation guinea pig model
(% in the total fatty acids, mean ± standard deviation)

| Time elapsed after exposure to UV-B | Control diet (N = 12) | # DGLA diet (N = 13) |
|---|---|---|
| 1 hour later | 1.8 ± 0.5 | *1.3 ± 0.4 |
| 3 hours later | 2.2 ± 0.5 | 1.9 ± 0.6 |
| 24 hours later | 1.7 ± 0.8 | 1.4 ± 0.7 |
| 48 hours later | 1.5 ± 0.8 | 1.2 ± 0.8 |

*$p < 0.05$ (Mann-Whitney U test vs. the control diet group)
: This DGLA diet contained the amount of free DGLA corresponding to about 0.08% in the diet.

Example 4

In order to investigate whether the ingestion of DGLA may have any effect on eosinophils, a triglyceride SUNTGD, a DGLA lipid having DGLA as the main constituent fatty acid, that was prepared according to a method described in Japanese Patent NO. 3354581 was used to examine its usefulness in experimental animals. This time, as an animal model that is closely related to eosinophil infiltration and increased cell counts, NC/Nga mice were used. Since this animal model has been recognized to be one of the most useful models of atopic dermatitis at present, and steroid external preparations and immunosuppressive external preparations currently used in the clinical setting for the treatment of atopic dermatitis have been demonstrated to be effective in this animal model too, it has been widely used in screening of therapeutic agents for atopic dermatitis.

Under a conventional feeding environment, mice are known to spontaneously develop dermatitis at about 8 weeks after birth, and then inflammation aggravates to a chronic type with the passage of days, and develops a human atopic dermatitis-like symptom both macroscopically and histopathologically. As characteristics of this pathological condition, there can be mentioned increased serum IgE accompanied by the onset of dermatitis and marked infiltration of immunocompetent cells such as mast cells, eosinophils and T cells at the lesion.

In this study, male or female NC/Nga mice were prepared and two groups of seven animals per group were used in a conventional feeding environment. The following two types of diets shown in Table 7 were prepared, and were fed ad libitum at post-ablactation week 5, and until the completion of the study at week 12. The groups comprised a control diet group and a DGLA diet group, and SUNTGD, a triglyceride having DGLA as the main constituent fatty acid, was added to the latter groups diet at about 1.0% DGLA (calculated as the amount of free fatty acids). Since the mean body weight of the mice was 20 g and the mean daily diet ingestion was about 2 g, the amount ingested of DGLA in this experiment was estimated to be about 1000 mg/kg per day for the DGLA group. Also, the amount of total fatty acids in the diet was adjusted to be 5% in both groups. Items evaluated were the macroscopic score of dermatitis symptoms under a blinded condition, the number of times of scratchings and IgE in the blood.

The animals were dissected upon completion of the experiment at week 12 to remove the skin at the back of the neck which was a dermatitis lesion, and then the tissue was fixed in a neutral buffered formalin solution and embedded in paraffin to prepare sliced sections, which were subjected to Luna stain to identify eosinophils. From these tissue samples, three samples out of seven per group were selected, and for a total of six samples, the degree of eosinophil infiltration was relatively evaluated. The method of selecting samples showed three samples that exhibited a value close to the mean macroscopic score of the dermatitis symptoms of each group were selected. The relative evaluation was made under a blinded condition so that the rater cannot identify the sample he/she is evaluating. The evaluation criteria of the degree of eosinophil infiltration was as follows:

++: Specifically severe eosinophil infiltration is confirmed at several spots and infiltration is also severe as a whole;

+−: Eosinophil infiltration is confirmed at a few spots or almost nothing.

As a result, without exhibiting any aberration in body weight changes (Table 8) and general findings, the DGLA diet group exhibited a tendency to suppress the number of eosinophils infiltrating into the skin lesion compared to the control diet group as shown in Table 9. Furthermore, at this time, alleviation in the macroscopic score of the dermatitis symptoms (the control diet group: 9.1±1.0, the DGLA diet group: 3.0±0.5), suppression of the number of times of scratching (the control diet group: 51.7±9.1 times, the DGLA diet group: 35.0±7.1 times), suppression of the amount of plasma IgE produced (the control diet group: 64.2±39.8 μg/ml, the DGLA diet group: 29.8±21.0 μg/ml) were also confirmed. The above results suggest that ingestion of DGLA may be very useful for various diseases that are closely related to eosinophil infiltration and increased cell count.

TABLE 7

Table of ingredients in each diet (unit: %)

| Ingredient (%) | Control diet | DGLA diet |
|---|---|---|
| Casein | 20.0 | 20.0 |
| DL-methionine | 0.3 | 0.3 |
| Cornstarch | 45.0 | 45.0 |
| Pregelatinized cornstarch | 10.0 | 10.0 |
| Sucrose | 10.0 | 10.0 |
| Cellulose powder | 5.0 | 5.0 |
| AIN76 mineral mix | 3.5 | 3.5 |
| AIN76 vitamin blend | 1.0 | 1.0 |
| Choline bitartarate | 0.2 | 0.2 |
| Corn oil | 3.34 | 0.84 |
| Lard oil | 1.67 | 0.42 |
| SUNTGD(*1) | 0.00 | (*2)2.50 |
| Olive oil | 0.00 | 1.25 |
| Total | 100.0 | 100.0 |

(*1)A triglyceride in which about 40% of the constituent fatty acids is DGLA.
(*2)Corresponding to about 1.0% in the diet as the amount of free DGLA.

TABLE 8

Changes in body weight of NC/Nga mice (g, mean ± standard deviation, N = 7)

| Week-old | Control diet group | DGLA diet group |
|---|---|---|
| 6 week-old | 20.4 ± 3.7 | 20.0 ± 2.4 |
| 9 week-old | 21.9 ± 3.1 | 22.9 ± 2.5 |
| 12 week-old | 23.2 ± 3.8 | 25.4 ± 3.2 |

TABLE 9

Degree of eosinophil infiltration in the skin at the back of the neck of NC/Nga mice

| | Sample I.D. | Degree of eosinophil infiltration |
|---|---|---|
| Control diet group | Sample 1 | ++ |
| | Sample 2 | ++ |
| | Sample 3 | ++ |
| DGLA diet group | Sample 4 | +− |
| | Sample 5 | +− |
| | Sample 6 | +− |

Evaluation criteria of the degree of eosinophil infiltration:
++: Specifically severe eosinophil infiltration is confirmed at several spots and infiltration is also severe as a whole;
+−: Eosinophil infiltration is confirmed at a few spots or almost nothing.

As described above, eosinophil infiltration can be inhibited by DGLA.

Example 5

In order to investigate whether ingestion of DGLA may have any effect on increased mast cell count, a triglyceride SUNTGD, a DGLA lipid having DGLA as the main constituent fatty acid, that was prepared according to a method described in Japanese Patent No. 3354581, was used to examine its usefulness in experimental animals. This time, as an animal model that is closely related to increased mast cell count, NC/Nga mice were used. Since this animal model has been recognized to be one of the most useful models of atopic dermatitis at present, and steroid external preparations and immunosuppressive external preparations currently used in the clinical setting for the treatment of atopy have also been demonstrated to be effective in this animal model, it has been widely used in screening of therapeutic agents for atopic dermatitis.

Under a conventional feeding environment, mice are known to spontaneously develop dermatitis at about 8 weeks after birth, and then inflammation aggravates to a chronic type with the passage of days, and develops a human atopic dermatitis-like symptom both macroscopically and histopathologically. As characteristics of this pathological condition, there can be mentioned increased serum IgE accompanied by the onset of dermatitis, differentiation and proliferation of mast cells at the lesion, and marked infiltration of immunocompetant cells, such as eosinophils and T cells at the lesion.

In this study, male or female NC/Nga mice were prepared and two groups of seven animals per group were used in a conventional feeding environment. The following two types of diets shown in Table 10 were prepared, and were fed ad libitum at post-ablactation week 5, and until the completion of the study at week 12. The groups comprised a control diet group and a DGLA diet group, and SUNTGD, a triglyceride having DGLA as the main constituent fatty acid, was added to the latter groups diet and adjusted to be about 1.0% DGLA (calculated as the amount of free fatty acids). Since the mean body weight of the mice was 20 g and the mean daily diet ingestion was about 2 g, the amount ingested of DGLA in this experiment was estimated to be about 1000 mg/kg per day for the DGLA group. Also, the amount of total fatty acids in the diet was adjusted to be 5% in both groups. Items evaluated were the macroscopic score of dermatitis symptoms under a blinded condition, the number of times of scratchings, and IgE in the blood.

The animals were dissected upon completion of the experiment at week 12 to remove the skin at the back of the neck, which was a dermatitis lesion, and then the tissue was fixed in a neutral buffered formalin solution, and embedded in paraffin to prepare sliced sections, which were subjected to toluidine blue stain to identify mast cells. From these tissue samples, two samples out of seven per group were selected, and for a total of four samples, the mast cell count and the degree of the cell count was evaluated. The method of selecting samples was that two samples that exhibited a value close to the mean macroscopic score of the dermatitis symptoms of each group were selected. In order to count the number of mast cells, the number of mast cells confirmed under microscopic examination at 10×40 fold magnification were counted, and the counting was repeated five times at different fields for the same sample, and the mean thereof was designated as the mast cell count.

For the relative evaluation of mast cell count, the mast cell count in the sample as a whole was evaluated. The relative evaluation criteria was as follows:

++: Extremely abundant mast cells are confirmed at several spots, and abundant as a whole;

+: Abundant mast cells are confirmed at a few spots, and slightly abundant as a whole;

+−: Mast cells are at an approximately normal level.

Counting of the number of mast cells and the relative evaluation of the cell count were made under a blinded condition so that the rater cannot identify the sample he/she is evaluating.

As a result, without exhibiting any aberration in body weight changes (Table 11) and general findings, the DGLA diet group exhibited a tendency to suppress the number of mast cells in the skin lesion compared to the control diet group as shown in Table 12. Furthermore, at this time, alleviation in the macroscopic score of the dermatitis symptoms (the control diet group: 9.1±1.0, the DGLA diet group: 3.0±0.5), suppression of the number of times of scratching (the control diet group: 51.7±9.1 times, the DGLA diet group: 35.0±7.1 times), suppression of the amount of plasma IgE produced (the control diet group: 64.2±39.8 µg/ml, the DGLA diet group: 29.8±21.0 µg/ml) were also confirmed. The above result suggests that the ingestion of DGLA may be very useful for various diseases that are closely related to increased mast cell counts such as atopic dermatitis, bronchial asthma, and allergic rhinitis.

TABLE 10

Table of ingredients in each diet (unit: %)

| Ingredient (%) | Control diet | DGLA diet |
|---|---|---|
| Casein | 20.0 | 20.0 |
| DL-methionine | 0.3 | 0.3 |
| Cornstarch | 45.0 | 45.0 |
| Pregelatinized cornstarch | 10.0 | 10.0 |
| Sucrose | 10.0 | 10.0 |
| Cellulose powder | 5.0 | 5.0 |
| AIN76 mineral mix | 3.5 | 3.5 |
| AIN76 vitamin blend | 1.0 | 1.0 |
| Choline bitartarate | 0.2 | 0.2 |
| Corn oil | 3.34 | 0.84 |
| Lard oil | 1.67 | 0.42 |
| SUNTGD(*1) | 0.00 | (*2)2.50 |
| Olive oil | 0.00 | 1.25 |
| Total | 100.0 | 100.0 |

(*1)A triglyceride in which about 40% of the constituent fatty acids are DGLA.
(*2)Corresponding to about 1.0% in the diet as the amount of free DGLA.

TABLE 11

Changes in body weight of NC/Nga mice (g, mean ± standard deviation, N = 7)

| Week-old | Control diet group | DGLA diet group |
|---|---|---|
| 6 week-old | 20.4 ± 3.7 | 20.0 ± 2.4 |
| 9 week-old | 21.9 ± 3.1 | 22.9 ± 2.5 |
| 12 week-old | 23.2 ± 3.8 | 25.4 ± 3.2 |

TABLE 12

Number of mast cells in the skin at the back of the neck of NC/Nga mice and relative evaluation

| | Sample I.D. | Mast cell count (*1) | Relative evaluation (*2) |
|---|---|---|---|
| Control diet group | Sample 1 | 33.2 | ++ |
| | Sample 2 | 37.4 | ++ |
| DGLA diet group | Sample 3 | 17.4 | + |
| | Sample 4 | 13.0 | +− |

(*1) Mast cell count: The number of mast cells confirmed in a field at 10 × 40 fold magnification. The counting was repeated five times at different fields for the same sample, and the mean thereof is expressed.
(*2) Relative evaluation criteria for mast cell count: ++: Extremely abundant mast cells are confirmed at several spots, and abundant as a whole; +: Abundant mast cells are confirmed at a few spots, and slightly abundant as a whole; +−: Mast cells are at an approximately normal level.

INDUSTRIAL APPLICABILITY

In the examination of the effect of DGLA ingestion for atopic dermatitis, DGLA can prevent dermatitis at lower doses than GLA, and is thus more useful in food for preventing atopic dermatitis. Furthermore, ingestion at the most appropriate dose is extremely important for usefulness.

Since the effect of oral ingestion of DGLA for inhibiting eosinophil infiltration is more effective than other PUFAs, DGLA is more useful in various diseases closely related to eosinophil infiltration and increased cell count, such as skin diseases, respiratory system diseases and digestive system diseases compared to other PUFAs.

Since oral ingestion of DGLA can suppress increased mast cell count very safely and effectively, DGLA is highly useful in various diseases closely related to increased mast cell count, such as skin diseases, asthma and rhinitis.

What is claimed is:

1. A method for treating atopic dermatitis in an individual, consisting essentially of administering dihomo-γ-linolenic acid (DGLA) to the individual in an amount sufficient to treat skin diseases in the individual, wherein said DGLA is derived from a microorganism, and wherein DGLA is administered at an amount of 5 mg-150 mg per adult per day.

2. The method of claim 1, wherein the DGLA is in a food or beverage, or a pharmaceutical composition.

3. The method of claim 2, wherein said pharmaceutical composition is in the form of a solution, a pill, a tablet or a capsule.

4. The method of claim 1, wherein said dihomo-γ-linolenic acid (DGLA) is in the form of a glyceride, a phospholipid, a glycolipid, an alkylester, or a free fatty acid or a salt thereof.

5. The method of claim 4, wherein said glyceride is a triglyceride, a diglyceride, or a monoglyceride.

6. The method of claim 1, wherein the individual has a low dihomo-γ-linolenic acid (DGLA) level.

7. The method of claim 6, wherein the individual having a low dihomo-γ-linolenic acid (DGLA) level has dysfunctional Δ6 desaturase and/or carbon chain elongase, has insufficient Δ6 desaturase and/or carbon chain elongase, or lacks Δ6 desaturase and/or carbon chain elongase.

8. The method of claim 2, wherein the food or beverage is baby food.

9. The method of claim 1, wherein DGLA is administered at an amount of 100 mg-150 mg per adult per day.

* * * * *